United States Patent [19]

Ericson et al.

[11] Patent Number: 5,569,194
[45] Date of Patent: Oct. 29, 1996

[54] DEVICE FOR PERMANENT CONNECTION BETWEEN AN ABDOMINAL WALL AND AN ABDOMINAL CAVITY

[76] Inventors: Lars Ericson, Prinsgatan 4B, Göteborg; Peter Thomsen, Hängestensvägen, Västra Frölunda, both of Sweden

[21] Appl. No.: 162,208
[22] PCT Filed: Jun. 23, 1992
[86] PCT No.: PCT/SE92/00452
§ 371 Date: Dec. 8, 1993
§ 102(e) Date: Dec. 8, 1993
[87] PCT Pub. No.: WO93/01844
PCT Pub. Date: Feb. 4, 1993

[30] Foreign Application Priority Data

Jul. 15, 1991 [SE] Sweden .................................. 9102181

[51] Int. Cl.⁶ .................................................. A61M 11/00
[52] U.S. Cl. ............................. 604/93; 623/11; 604/890.1
[58] Field of Search ........................... 604/890.1–892.1, 604/93, 175, 244, 280, 281, 29, 49; 623/66, 1; 606/151; 128/DIG. 6, 26

[56] References Cited

U.S. PATENT DOCUMENTS

| | | | |
|---|---|---|---|
| 4,490,137 | 12/1984 | Moukheibir | 604/175 |
| 4,781,694 | 11/1988 | Branemark et al. | 606/151 |
| 4,886,501 | 12/1989 | Johnson et al. | 604/93 |
| 4,911,717 | 3/1990 | Gaskill et al. | 604/891.1 |
| 4,946,444 | 8/1990 | Heimke et al. | 604/175 |
| 5,213,574 | 5/1993 | Tucker | 604/93 |

FOREIGN PATENT DOCUMENTS

| | | |
|---|---|---|
| 0164896 | 12/1985 | European Pat. Off. . |
| 0194980 | 9/1986 | European Pat. Off. . |
| 462416 | 6/1990 | Sweden . |

OTHER PUBLICATIONS

NY Teknik –Tidskrift, vol. 46, 1991, Jan Melin: "Insulin-pump ersatter dagliga injektioner," p. 4. (with translation).

*Primary Examiner*—Robert A. H. Clarke
*Attorney, Agent, or Firm*—Lerner, David, Littenberg, Krumholz & Mentlik

[57] ABSTRACT

The invention relates to a structure for bringing about a permanent connection between the abdominal wall and the abdominal cavity of humans and animals. The structure is intended for the supply of medicines to the abdominal cavity in a predetermined and controlled way and it includes an anchoring plate (8) intended to be anchored in the abdominal cavity wall, and it carries a hollow projecting conduit stud (5) which is intended to open out into the abdominal cavity (2) and which has a smooth anti adhesive surface of polished or anodically oxidized titanium.

17 Claims, 1 Drawing Sheet

5,569,194

DEVICE FOR PERMANENT CONNECTION BETWEEN AN ABDOMINAL WALL AND AN ABDOMINAL CAVITY

TECHNICAL FIELD

The present invention relates to a means for bringing about a permanent connection between the abdominal wall and the abdominal cavity of living beings. The means consists of an implant and is intended to administrate medicines into the abdominal cavity.

PRIOR ART

Since a few years one has implanted different objects in the body intended to facilitate some functions of the body, support body parts or emit medicines in desired doses. Examples of such implants are the so called pacemaker, prosthesis and nails in bones, anchoring elements for artificial teeth and supply arrangements for medicines to the soft parts of the body.

One such example of a supply means for medicines or liquids to the soft parts of the body is described in the Swedish patent 8500946-2. At this device one has brought about a permanent passage in the abdominal wall into the abdominal cavity and the arrangement comprises substantially an anchoring plate of titanium in the abdominal wall having a conduit connection outwardly and inwardly through which one has introduced a hose of silicone for supplying the medicine or the liquid to the proper place in the abdominal cavity.

Electronically controlled pumps having a reservoir of medicines intended to in a predetermined way give an adapted amount of medicines via pipes or channels in the body are also known implants. Deceases which can be treated by means of such implants are inter alia diabetes.

With regard to the treatment of diabetes the use of insulin has during the last decade become more and more individually directed with the aim to obtain a dose of insulin which is optimal for each person taking into account the food intake and the activity. The importance of individually adapted administration in the form of injection has great influence for the minimizing of complications inter alia in the form of vascular and nerve lesions, which can occur for patients having diabetes and which for example can result in impaired vision and limb discomforts. An administration of insulin which is coupled to the need of the patient and which is conducted by the patient or the doctor is then to be regarded as an improvement over the present injection technique. Such an improved technique is to release the medicine from an in the body of the patient implanted reservoir for insulin. It is thus when using such a reservoir with automatic administration of the insulin necessary that the device which makes the work does not change with time so that the supply of medicine also automatically changes in a not desired way. It is above all important that the opening of the cannula, the hose or the pipe which are used are not clogged by the tissue of the body which is growing firmly connected in the device. In connection with implants it must be further regarded that those materials which are used are compatible with the body of man. This means that the materials may not cause inflammation or negative reaction of the tissues in a not desired degree or stimulate the break out of infections. Such a reaction can result in that tissue is growing over the implant or is fastened in it. It is therefore of greatest importance that suitable materials are chosen in the implant.

THE TECHNICAL PROBLEM

It has therefore since long been a desire that at administration of medicines in the abdominal cavity bring about a device in the shape of a reservoir for the medicines in the abdominal wall which is permanently fastened in the tissue and accordingly does not move in abdominal wall, which device comprises an irritation free passage of a conduit stud or the like between the abdominal wall and the abdominal cavity and which makes it sure that the effluent function of the medicine into the abdominal cavity does not change or is not disturbed by overgrowing of tissue over the pipe outlet. This latter phenomena with overgrowing and clogging of the outlet has been a large problem at the known devices.

THE SOLUTION

Through the present invention one has solved the problems at the known devices and satisfied the wishes put on them by bringing about a device for a permanent connection between the abdominal wall and the abdominal cavity of humans and animals which is characterized in that it comprises an anchoring plate intended to be anchored in the abdominal wall, carrying a hollow projecting conduit stud intended to open out into the abdominal cavity which conduit stud shall consist of pure titanium or have a surface layer of pure titanium with a polished or anodically oxidized smooth anti adhesive surface.

According to the invention the conduit stud can also consist of plastics or some other material but then being covered by pure titanium. That part of the conduit stud which is closest to the anchoring plate can however have a rougher, machined surface. It is also possible according to the invention to arrange a plastic hose for the medicines within the conduit stud.

According to the invention the anchoring plate should consist of pure titanium. This should have a surface which is machined. It is also possible according to the invention to use other materials, for instance metals such as zirconium or alloys of titanium or polymers such as silicone or polytetrafluoroethylene.

According to the invention the anchoring plate itself may consist of a medicine reservoir which is provided with means for automatic and controlled supply of medicines to the abdominal cavity through the conduit stud.

It is according to the invention also possible to arrange a separate medicine reservoir having means for automatic and controlled supply of medicines to the cavity and which is connected to the anchoring plate and the conduit stud.

DETAILED DESCRIPTION OF THE FIGURES

Figure 1:
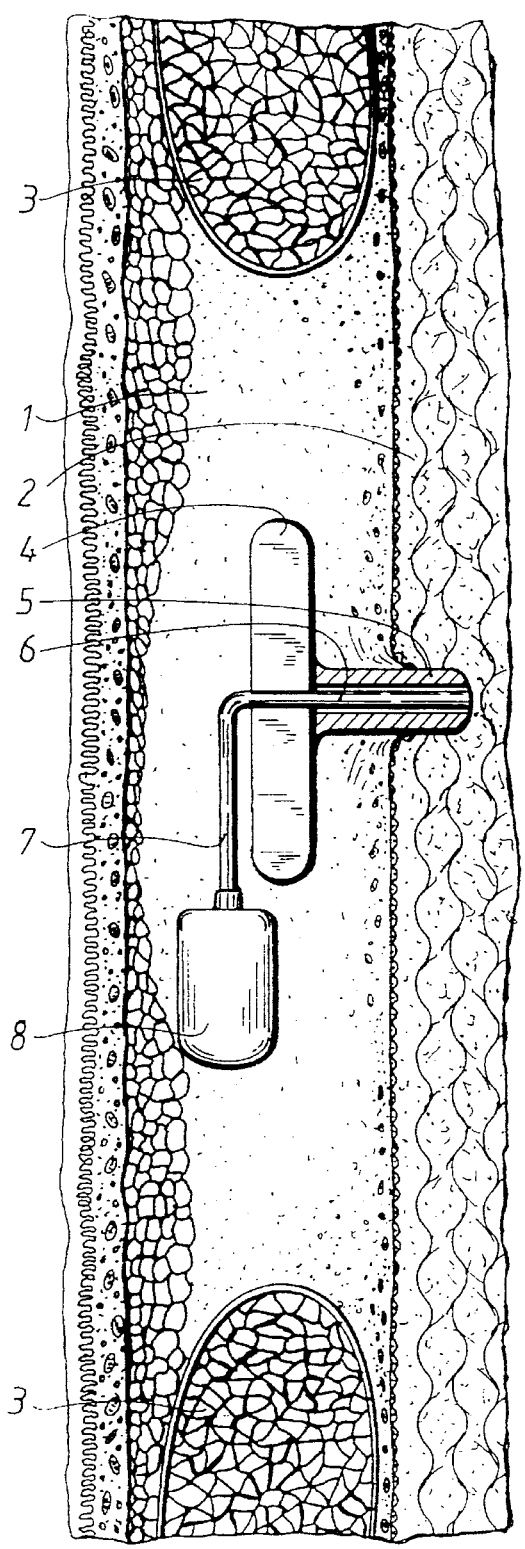
Figure 2:
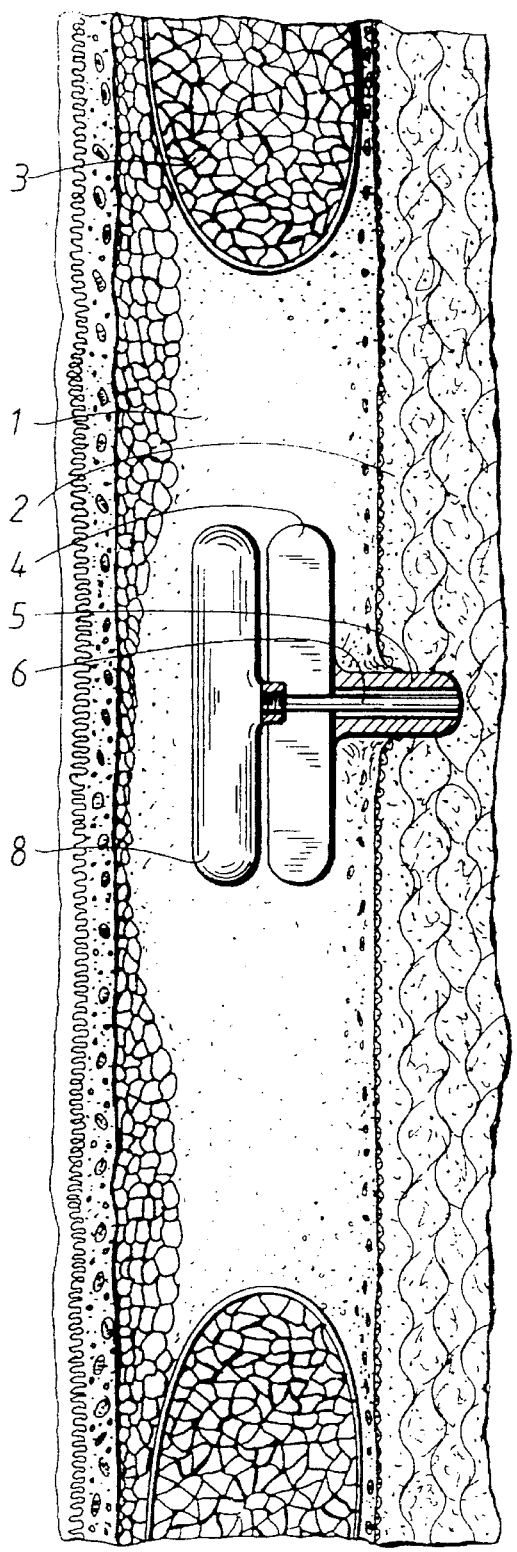

The invention will be further described in the following in connection with the attached drawings where FIG. 1 shows a device partly in section according to the invention implanted in an abdominal wall, and FIG. 2 shows also partly in section another embodiment of the invention.

PREFERRED EMBODIMENTS

FIG. 1 shows the abdominal wall 1 with the abdominal cavity 2 inside. In the abdominal wall, muscle tissues 3 are indicated. The anchoring plate 4 according to the invention has as is visible been operated into the abdominal wall. This carries a conduit stud 5 which penetrates the abdominal wall 1 and into the abdominal cavity 2. This conduit stud 5 is provided with a hole 6 that via a hose 7 is connected to a medicine reservoir 8. This medicine reservoir 8 is known per see and comprises besides medicines also an electronically controlled pump which pumps medicines in desired degree, This medicine reservoir is therefore not included in the present invention.

The anchoring plate 4 which should be disc shaped can be provided with through going holes for facilitating the anchoring in the abdominal wall but it can have any suitable shape. It must however be rounded so that it does not press pointwise on the surrounding tissue at any place. The material in the anchoring plate 4 should be pure titanium. This material has in different connections shown to be very suitable to be used in implants. It is however important that the surface of this anchoring plate has a proper structure for good anchoring of tissue and it should therefore be machined for example by turning and have a surface corresponding to a $R_z$ number in the order of size of 3. Such a titanium plate is compatible with the surrounding tissue and the tissue will be connected to this without any appreciable medical complications.

Even though the anchoring plate 4 as described above advantageously should consist of titanium having a machined surface it is however not excluded that it can also consist of even other with the body compatible materials such as zirconium, titanium alloyed with for example aluminium and vanadium and polymers such as polytetrafluoroethylene (PTFE) and silicone.

The conduit stud 5 that shall project into the abdominal cavity should also be well rounded without any sharp corners. The material in this conduit stud shall as said above be titanium but in this case the surface of the titanium shall not only be turned but polished and/or anodically oxidized. That part of the conduit pipe 5 which is closest to the anchoring plate 4 and which passes the peritoneum can also consist of machined titanium. This will cause that the tissue around the conduit stud is not fastened to this and around it so that the pipe outlet is clogged or narrowed. This is of utmost importance as the administration of medicines that shall come from the reservoir 8 is predetermined and should be disturbed if the outlet is clogged or narrowed. Instead of a conduit stud 5 one can use a plastic hose of for example silicone but this should then be covered with titanium of the above mentioned kind for preventing of being overgrown. This is especially important in the vicinity of the outlet. The channel 6 in the conduit stud 5 can be directly connected to the reservoir 8 in some way and thus be an outlet channel for medicines but it can also comprise a hose which goes directly from the medicine reservoir 8 and out to the outlet. This hose is then protected by the titanium pipe 5. The length of the conduit stud 5 in the abdominal cavity can be adapted in dependence of the sickness that is to be treated by the medicine that shall be administered and of the actual anatomic conditions but a length of up to a couple of centimeters is suitable.

FIG. 2 shows another embodiment of the invention than the one which is shown in FIG. 1. According to this latter embodiment the medicine reservoir 8 is arranged directly outside the anchoring plate 4. In this case it is suitable that the reservoir 8 is screwed to the anchoring plate, the screwing should be performed by means of a pipe stud having outer threads so that a channel is formed directly from the reservoir 8 through the anchoring plate 4 and the conduit stud 5. In both of these embodiments the reservoir 8 can be removed and exchanged without touching the anchoring plate 4 and the conduit stud 5. This can be an advantage if something wrong arises with the reservoir 8 itself including the pump arrangement while the rest of the device is in order.

A third embodiment can also be that one makes the anchoring plate 4 and the reservoir 8 as a unit with attached conduit stud 5. This is a simplified construction with a more compact design but one must in such a case when possible function errors arise take the whole device out.

Through the present invention one has obtained the advantage that one has brought about a device having an anchoring part which can be of different design and which can be exchanged and which will be fastened to the tissues as they grow without complications and a supply part for medicines into the abdominal cavity which is compatible with the surrounding tissue and which by its anti adhesive surface prevents overgrowing by surrounding tissue resulting in narrowing or clogging of the outlet. This will give the whole administration system for medicines a longer functional time. This advantage is increased also therethrough that it is according to the invention possible to exchange parts of the system if necessary.

The invention is not limited to the embodiment examples shown but it can be varied in different ways within the scope of the claims.

We claim:

1. A device providing a permanent connection between an abdominal wall and an abdominal cavity of humans or animals, comprising:

an anchoring plate adapted for anchoring within said abdominal wall, a conduit having an opening extending therethrough, said conduit projecting outwardly from said anchoring plate and having a free end for penetrating into said abdominal cavity, said opening adapted for receiving a hose for delivery of a medication to said abdominal cavity by passing through and being supported by said opening in said conduit, and a reservoir containing said medication for delivery through said hose to said abdominal cavity, said conduit having at least an outer surface of pure titanium, whereby growth of tissue surrounding said device into said conduit and clogging of said conduit and hose are prevented.

2. The device of claim 1, wherein said entire conduit is formed of said pure titanium.

3. The device of claim 1, wherein said outer surface of pure titanium is polished or anodically oxidized for smoothness.

4. The device of claim 1, wherein to further prevent growth of said surrounding tissue into said device, said entire anchoring plate is made of said pure titanium.

5. The device of claim 1, wherein said reservoir includes an arrangement for automatic and controlled supply of said medication to said abdominal cavity through said conduit.

6. The device of claim 5, wherein said reservoir is connected to said anchoring plate and said conduit.

7. The device of claim 1, wherein said anchoring plate is made of a material selected from the group consisting of titanium, zirconium, a titanium alloy, a polymer and silicone.

8. The device of claim 7, wherein said polymer is polytetrafluoroethylene.

9. The device of claim 1, wherein said conduit is made out of silicone, at least a part of said outer surface of said conduit being covered with said pure titanium.

10. The device of claim 1, wherein an outside surface of said free end of the conduit is polished or anodically oxidized for smoothness.

11. The device of claim 1, wherein said entire anchoring plate is made of said pure titanium.

12. A device providing a permanent connection between an abdominal wall and abdominal cavity of humans or animals, comprising:

an elongated anchoring plate, said elongated anchoring plate being positioned within said abdominal wall in such a manner that a longitudinal axis of said anchoring plate extends along a border between said abdominal wall and said abdominal cavity, a conduit have an opening extending therethrough, said conduit projecting outwardly from said anchoring plate in the direction of said abdominal cavity and having a free end, a hose for delivery of a medication to said abdominal cavity, said hose passing through said opening in the conduit, at least a part of said hose situated outside said conduit in the vicinity of said anchoring plate, and a reservoir containing said medication positioned in the vicinity of said anchoring plate for supplying said medication to said hose, said conduit having at least said free end thereof formed of pure titanium, whereby growth of tissue surrounding said device into said conduit and clogging of said conduit and hose are prevented thereby.

13. The device of claim 12, wherein said entire conduit is formed of said pure titanium.

14. The device of claim 13, wherein at least a portion of said reservoir is supported by said anchoring plate.

15. A device for providing a permanent connection between an abdominal wall and an abdominal cavity of humans or animals comprising an anchoring plate adapted for anchoring within said abdominal wall, a conduit projecting outwardly from said anchoring plate including an opening extending therethrough, said conduit having a free end for penetrating into said abdominal cavity, and a reservoir for containing medication and delivering said medication to said opening extending through said conduit for delivery to said abdominal cavity, said conduit including at least an outer surface comprising pure titanium whereby the growth of tissue surrounding said device into said conduit and clogging of said conduit are thereby prevented.

16. The device of claim 15 wherein said at least said outer surface of said conduit comprises polished or anodically oxidized pure titanium.

17. The device of claim 15 wherein said anchoring plate comprises a material selected from the group consisting of titanium, zirconium, titanium alloys, polymers and silicone.

* * * * *

UNITED STATES PATENT AND TRADEMARK OFFICE
CERTIFICATE OF CORRECTION

PATENT NO. : 5,569,194

DATED : October 29, 1996

INVENTOR(S) : Lars Ericson and Peter Thomsen

It is certified that error appears in the above-identified patent and that said Letters Patent is hereby corrected as shown below:

Column 1, line 27, delete "wail" and insert therefor --wall--.
Column 6, line 3, delete "13" and insert therefor --12--.

Signed and Sealed this

Seventh Day of January, 1997

Attest:

BRUCE LEHMAN

*Attesting Officer*   Commissioner of Patents and Trademarks